United States Patent [19]

Kishino et al.

[11] 4,005,197
[45] Jan. 25, 1977

[54] COMBATING INSECTS, ACARIDS AND NEMATODES WITH S-ALKOXYETHYL-PHENYL-DI- AND TRI-THIOPHOSPHONIC ACID ESTERS

[75] Inventors: Shigeo Kishino, Tokyo; Akio Kudamatsu, Kanagawa; Shozo Sumi, Tokyo, all of Japan

[73] Assignee: Bayer Aktiengesellschaft, Leverkusen, Germany

[22] Filed: Apr. 23, 1975

[21] Appl. No.: 570,972

Related U.S. Application Data

[62] Division of Ser. No. 344,799, March 26, 1973, Pat. No. 3,894,124.

[30] Foreign Application Priority Data

Apr. 6, 1972    Japan ................. 47-33844

[52] U.S. Cl. ................. 424/216; 424/217
[51] Int. Cl.² ................. A01N 9/36
[58] Field of Search ............ 424/216, 217

[56] References Cited

UNITED STATES PATENTS 3,798,292   3/1974   Kishino et al. ............ 424/216
3,839,509   10/1974  Drabek et al. ............ 424/216

FOREIGN PATENTS OR APPLICATIONS 1,954,894   5/1971   Germany

*Primary Examiner*—V. D. Turner
*Attorney, Agent, or Firm*—Burgess, Dinklage & Sprung

[57] ABSTRACT

S-alkoxyethyl-phenyl-di- and -tri-thiophosphonic acid esters of the formula

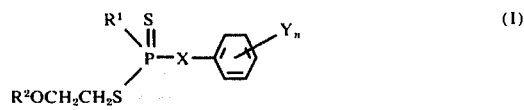

in which
  $R^1$ and $R^2$ each independently is $C_1$-$C_6$ alkyl,
  X is oxygen or sulfur,
  Y is $C_1$-$C_6$ alkyl, $C_1$-$C_6$ alkylmercapto or halogen, and
  $n$ is 1 or 2, which possess insecticidal, acaricidal and nematocidal properties.

11 Claims, No Drawings

COMBATING INSECTS, ACARIDS AND NEMATODES WITH S-ALKOXYETHYL-PHENYL-DI- AND TRI-THIOPHOSPHONIC ACID ESTERS

This is a division of application Ser. No. 344,799, filed Mar. 26, 1973, now U.S. Pat. No. 3,894,124 issued July 8, 1975.

The present invention relates to and has for its objects the provision of particular new S-alkoxyethyl-phenyl-di- and tri-thiophosphonic acid esters, i.e. S-alkoxyethyl-O- or S-(optionally-substituted)-phenyl-di- and tri-thiophosphonic acid esters, which possess insecticidal, acaricidal and nematocidal properties, active compositions in the form of mixtures of such compounds with solid and liquid dispersible carrier vehicles, and methods for producing such compounds and for using such compounds in a new way especially for combating pests, e.g. insects, acarids and nematodes, with other and further objects becoming apparent from a study of the within specification and accompanying examples.

In Japanese Patent Publication Specification No. 24874/63, there are disclosed dithiophosphonic acid esters of the formula

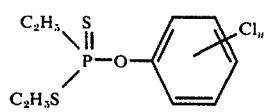

in which
n is 1, 2 or 3,
which are known to have insecticidal activity.

In German Pat. No. 1,954,894, there are disclosed dithiophosphonic acid esters of the formula

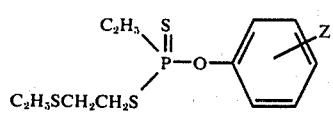

in which
Z is Cl or —SCH$_3$, which are also known to have insecticidal activity.

The present invention provides di- and trithiophosphonic acid esters of the general formula

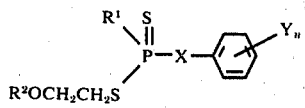

in which
R$^1$ and R$^2$ each independently is C$_1$-C$_6$ alkyl,
X is oxygen or sulfur,
Y is C$_1$-C$_6$ alkyl, C$_1$-C$_6$ alkylmercapto or halogen, and
n is 1 or 2.

The compounds of the formula (I) have been found to exhibit excellent insecticidal, acaricidal and nematocidal properties. Compared with active compounds having a similar structure and compounds with a similar type of activity which have been described in the literature, the novel compounds according to the present invention show both a substantial improvement in effect and a very low toxicity towards warm-blooded animals; consequently, the present compounds are of great utility.

Preferably, R$^1$ and R$^2$ are each C$_1$-C$_4$ lower alkyl (i.e. methyl, ethyl, n- or isopropyl or n-, sec.-, iso- or tert.-butyl), and Y is C$_1$-C$_4$ lower alkyl-mercapto or halogen, the Y's being identical or different when n is 2.

The present invention also provides a process for the production of a compound of the formula (I) above in which (a) a 2-alkoxyethylmercaptan of the general formula $$R^2OCH_2CH_2SH \qquad (II)$$

is reacted, as such or in the form of a metal salt thereof, with an alkane-O(or S)-phenylthio(or dithio)-phosphonic acid chloride of the general formula

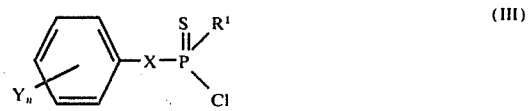

or (b) an alkane-O(or S)-phenyldithio(or trithio)-phosphonic acid of the general formula

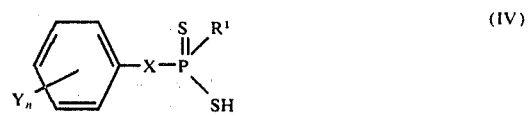

is reacted, as such or in the form of a metal, ammonium or substituted ammonium salt thereof, with a 2-alkoxyethyl halide or a 2-alkoxyethylsulfonic acid ester of the general formula $$Z-CH_2CH_2OR^2 \qquad (V).$$

in which formulas (II) – (V)
R$^1$, R$^2$, X, Y and n have the meanings stated above, and
Z is halogen or a sulfonic acid residue.

The process variant (a) is illustrated by the following equation:

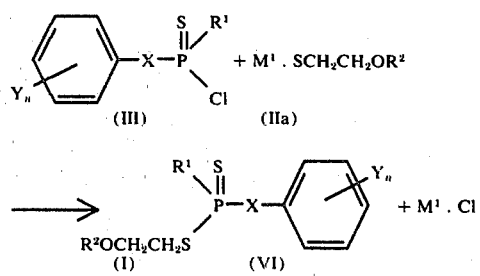

in which
M$^1$ is hydrogen or an alkali metal, preferably sodium or potassium.

As examples of the thio(or dithio)-phosphonic acid chlorides of the general formula (III), there may be mentioned:

methyl-O-(2,4-dichlorophenyl)-, ethyl-O-(2,4-dichlorophenyl)-,
methyl-S-(4-chlorophenyl)-, ethyl-S-(4-chlorophenyl)-, ethyl-O-(4-methylmercaptophenyl)-, and methyl-O-(2-chloro-4-tert-butylphenyl)-thiono (or dithio)-phosphonic acid chlorides.

As examples of the 2-alkoxyethylmercaptans of the general formula (II) and their salts, there may be mentioned:

2-ethoxyethylmercaptan, 2-iso-propoxyethylmercaptan, and their sodium or potassium salts.

The process variant (b) may be illustrated by the following equation:

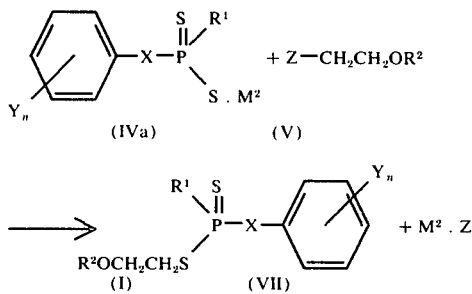

in which

M² is hydrogen, an alkali metal atom, preferably sodium or potassium, ammonium, triethylammonium, diethyl-anilinium or pyridinium, and Z is a chloro, bromo or iodo substituent or a p-toluene-sulfonic acid residue.

As examples of the dithio(or trithio)-phosphonic acids of the general formula (IV) and their salts, the following may be mentioned:

O-(2,4-dichlorophenyl)-methanedithiophosphonic acid, O-(2,4-dichlorophenyl)-ethanedithiophosphonic acid, S-(4-chlorophenyl)-methanetrithiophosphonic acid, S-(4-chlorophenyl)-ethanetrithiophosphonic acid, O-(4-methylmercaptophenyl)-ethanedithiophosphonic acid, O-(2-chloro-4-tert-butylphenyl)-methanedithiophosphonic acid and their potassium, sodium, ammonium, triethylammonium, diethylanilinium or pyridinium salts.

As examples of the 2-alkoxyethyl halides and 2-alkoxy-ethyl sulfonic acid esters of the general formula (V) there may be mentioned:

2-ethoxyethyl bromide, 2-iso-propoxyethyl bromide, and the corresponding chlorides, iodides and p-toluenesulfonic acid esters.

In the preparative process according to the present invention, it is preferred that use be made of a solvent or a diluent. For this purpose, all types of inert solvents and diluents can be used, especially water and inert organic compounds such as aliphatic, alicyclic and aromatic hydrocarbons which may be chlorinated, such as hexane, cyclohexane, petroleum ether, ligroin, benzene, toluene, xylene, methylene chloride, chloroform, carbon tetrachloride, mono-, di- and tri-chloroethylene, chlorobenzene; ethers, such as diethyl ether, methyl ethyl ether, di-isopropyl ether, dibutyl ether, ethylene oxide, dioxane and tetrahydrofuran; ketones, such as acetone, methyl ethyl ketone, methyl isopropyl ketone and methyl isobutyl ketone; nitriles, such as acetonitrile, propionitrile and acrylonitrile; alcohols, such as methanol, ethanol, isopropanol, butanol and ethylene glycol; esters, such as ethyl acetate and amyl acetate; acid amides, such as dimethylformamide and dimethylacetamide; sulfones and sulfoxides, such as dimethyl sulfoxide and sulfolane; and bases, such as pyridine.

When the 2-alkoxyethylmercaptan (II), in the case of process variant (a), or the alkane-O-(or S)-phenyldithio(or trithio)-phosphonic acid (IV), in the case of process variant (b), is reacted as such rather than in the form of a salt, use is generally made of an acid-binding agent. Any of the commonly used acid-binding agents may be used, such as alkali metal hydroxides, carbonates, bicarbonates and alcoholates, or tertiary amines, for example triethylamine, diethylaniline or pyridine.

The dithio(or trithio)-phosphonic acids of the formula (IV) may be prepared by known methods, for example by reacting the appropriate phenol or thiophenol with an alkane-thiophosphonic anhydride. The acid of the formula (IV) is generally isolated before it is used in the process of this invention, but it is also possible to react it in situ with the compound of the formula (V), i.e. without isolation thereof.

The process of this invention can be carried out at a temperature within a wide range. In general, the reaction (in either process variant) is effected at about −20° C to the boiling point of the reaction mixture, preferably at about 0° C to 100° C or to the boiling point of the reaction mixture, whichever is the lower. The reactions are generally effected at normal pressure, although it is possible to employ an elevated or reduced pressure.

Surprisingly, the compounds of the present invention exhibit, in addition to their marked acaricidal and nematocidal activity, a better activity against insects, especially Lepidoptera, than prior-art compounds such as those mentioned above that are disclosed in Japanese Patent Publication No. 24874/63 and in German Pat. No. 1954894.

The active compounds of this invention show no phytotoxicity, yet their pesticidal effects set in quickly and are long-lasting. In consequence, the present compounds can be used effectively for the control of a wide range of pests, such as sucking insects, biting insects, acarids and nematodes.

By way of example, insect pests from the Coleoptera include *Sitophilus oryzae, Tribolium ferrugineum, Epilachna sparsa orientalis, Agriotes fuscicollis* and *Anomala lucens;* the Lepidoptera include, for instance, *Porthetria dispar,* the tent caterpillar, the green caterpillar, *Prodenia litura,* the two-brooded rice-borer, *Adoxophyes privatana* and the almond moth; the Hemiptera include, for instance, *Hephotettix cincticeps, Nilaparvata lugens, Pseudococcus comstocki, Unaspis yanonensis, Nyzus persicae, Aphis pomi* Degeer, and *Rhopalosiphum psuedobrassicae;* the Orthoptera include, for instance, *Blatella germanica, Periplaneta americana* and *Gryllotalpa africana;* the Isoptera include, for instance, *Leucotermes speratus;* and the Diptera include, for instance, *Musca domestica, Aedes aegypti, Hylemya platura, Culex pipiens, Anopheles sinensis* and *Culex tritaeniorhynchus.*

Furthermore, as pests from the Acarina, there can be mentioned, for instance, *Tetranychus urticae, Panonychus citri* and *Aculops pelekassi;* while the Nematoda include, for instance, *Meloidogyne incognita*, *Aphelenchoides besseyi* and *Heterodera glycines*.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, wettable tablets, fumigating agents, smoking agents, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicle for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, ethylene chloride, etc.), alcohols (e.g. methanol, ethanol, propanol, butanol, glycol, etc.) as well as ethers and esters thereof (e.g. ethylene glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alimina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Various adjuvants may be used, for example stabilizers; spreaders (adhesives), such as agricultural soaps, calcium caseinate, sodium alginate, polyvinyl alcohol (PVA), detergents, coumarone or indene resins and polyvinyl butyl ether; combustive agents for fumigating, such as nitrites, zinc powder and dicyanodiamide; oxygen-yielding agents such as perchlorates and dichromates; phytotoxicity-reducing agents such as zinc sulfate, ferrous chloride and copper nitrate; effect-prolonging agents such as terphenyl chloride; dispersion stabilizers such as casein, gum tragacanth, carboxymethyl cellulose (CMC), polyvinyl alcohol; and synergistic agents.

In the formulations containing a compound of this invention, it is possible to include other agricultural chemicals such as insecticides, fungicides, acaricides, nematocides, antiviral agents, herbicides, plant-growth modifiers and attractants (which classes of materials include, for instance, organic phosphoric acid esters, carbamates, dithio- or thiolcarbamates, organic chlorine compounds, dinitro compounds, organosulfur or organometallic compounds, antibiotics, substituted diphenyl ethers, urea compounds and triazine compounds), as well as fertilizers.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplates those in which the active compound is present in an amount substantially between about 0.0001–20%, preferably 0.005–10%, by weight of the mixture. Thus, the present invention contemplates over-all compositions which comprises mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 3 to 1000 g/hectare, preferably 30 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects, acarids and nematodes, which comprises applying to at least one of correspondingly (a) such insects, (b) such acarids, (c) such nematodes, and (d) the corresponding habitat thereof, i.e. the locus to be protected, a correspondingly combative or toxic amount, i.e. an insecticidally, acaricidally or nematocidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, misting, injecting, coating, banding, powder-coating, covering, dipping, baiting, and the like.

It will be realized, of course, that the concentration of the particular active compound utilized in admixture with the carrier vehicle will depend upon the intended application. Therefore, in special cases it is possible to go above or below the aforementioned concentration ranges.

The synthesis, unexpected superiority and outstanding activity of the particular new compounds of the present invention are illustrated, without limitation, by the following examples:

EXAMPLE 1

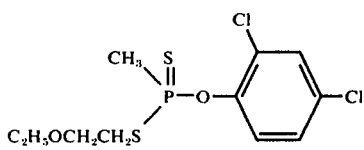
(1)

6.9 g of sodium were added to a mixture of 400 ml of toluene and 38 g of 2-ethoxyethyl mercaptan, and were dissolved by heating. While cooling the mixture, 83 g of O-(2,4-dichlorophenyl)-methane-thionophosphonyl chloride were added, and the mixture was refluxed for 3 hours. After the reaction, the mixture was washed with water and 1% sodium carbonate solution at room temperature, followed by drying over anhydrous sodium sulfate. The toluene was distilled off and 95 g of O-(2,4-dichlorophenyl)-S-(2-ethoxyethyl)-methane-phosphonodithioate were obtained; $n_D^{20} = 1.5847$.

The following compounds were synthesized using methods analogous to the one described above:

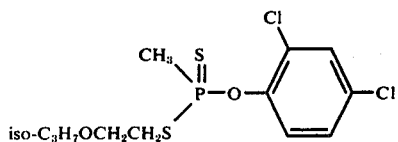
(2)

Refractive index $n_D^{20} = 1.5708$
Yield = 93%

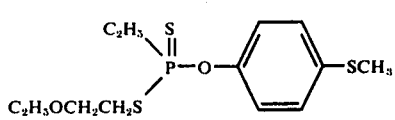
(3)

Boiling point = 158°–161° C/0.07 mm Hg
Refractive index $n_D^{20} = 1.5933$
Yield = 90%

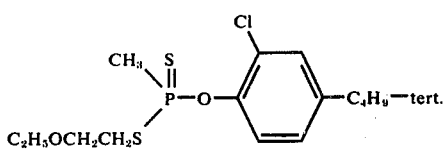
(4)

Refractive index = 1.5581
Yield = 91%

EXAMPLE 2

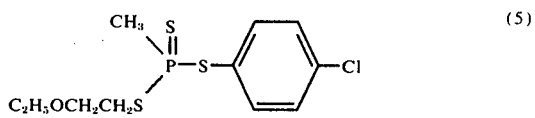
(5)

35.6 g of S-(4-chlorophenyl)-methane-trithiophosphonic acid triethylammonium salt were dissolved in 200 ml of acetonitrile, and 15.3 g of 2-ethoxyethyl bromide were added to the mixture, which was then refluxed for a period of 3 hours. After the completion of the reaction, the oil layer was extracted with benzene and large quantities of water; the benzene layer was washed with water and 1% sodium carbonate solution, followed by drying over anhydrous sodium sulfate.

The benzene was distilled off and 27.8 g of S-(4-chlorophenyl)-S-(2-ethoxyethyl)-methane-phosphonotrithioate were obtained; $n_D^{24} = 1.6157$.

EXAMPLE 3

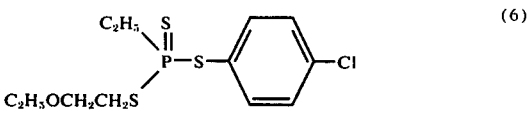
(6)

74 g of S-(4-chlorophenyl)-ethane-trithiophosphonic acid triethylammonium salt were dissolved in 200 ml of acetonitrile, and 48.8 g of 2-ethoxyethyl-p-toluenesulfonic acid ester were added to the mixture, which was then refluxed for 3 hours. After the completion of the reaction, the oil layer was extracted with benzene and large quantities of water; the benzene layer was washed with water and 1% sodium carbonate solution, followed by drying over anhydrous sodium sulfate.

The benzene was distilled off, and 56 g of S-(4-chlorophenyl)-S-(2-ethoxyethyl)-ethane-phosphonotrithioate were obtained; $n_D^{24} = 1.6049$.

EXAMPLE 4

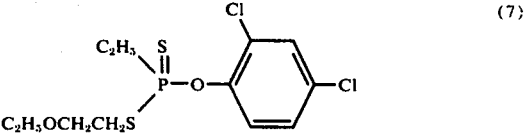
(7)

49.5 g of anhydrous ethanedithiophosphonic acid were suspended in acetonitrile, and 65 g of 2,4-dichlorophenol and 41 g of triethylamine dissolved in 200 ml of acetonitrile were added to the mixture while maintaining the reaction temperature at 10° C. After the addition, the mixture was agitated at 60° C for 2 hours. 61 g of 2-ethoxyethyl bromide were then added and then the reaction mixture was refluxed for 3 hours. After the completion of the reaction, the oil layer was extracted with benzene and large quantities of water; the benzene layer was washed with water and 1% sodium carbonate solution, followed by drying over anhydrous sodium sulfate.

The benzene was distilled off and 122 g of O-(2,4-dichlorophenyl)-S-(2-ethoxyethyl)-ethane-phosphonodithioate were obtained; $n_D^{20} = 1.5781$.

The pesticidal compositions of this invention are illustrated by the following Examples wherein parts are by weight

EXAMPLE 5

(Wettable Powder)

15 parts of compound No. 1, 80 parts of a mixture of diatomaceous earth and kaolin (1.5) and 5 parts of an emulsifying agent, "Runnox" (a polyoxyethylene alkyl aryl ether) were mixed and ground to form a wettable powder. This was diluted with water to a concentration of 0.03% before being applied by spraying.

EXAMPLE 6

(Emulsion)

30 parts of compound No. 7, 30 parts of xylene, 30 parts of "Kawakasol" (a methylnaphthalene) and 10 parts of "Sorpol" (a polyoxyethylene alkyl aryl ether) were mixed and agitated to form an emulsion. This was diluted with water to a concentration of 0.03% before being applied by spraying.

EXAMPLE 7

(Dust)

2 parts of compound No. 2, and 98 parts of a mixture of talc and clay (1:3) were ground and mixed to form a dusting agent.

EXAMPLE 8

(Dust)

1.5 parts of compound No. 6, 0.5 part of isopropyl hydrogen phosphate (PAP) and 98 parts of a mixture of talc and clay (1:3) were ground and mixed to form a dusting agent.

EXAMPLE 9

(Granules)

A mixture of 10 parts of compound No. 3, 10 parts of bentonite, 78 parts of a mixture of talc and clay (1:3) and 2 parts of lignin sulfonate was intimately mixed with 25 parts of water and the resultant mixture was finely comminuted into 20–40 mesh particles by means of an extrusion-type granulator. The product was dried at 40°–50° C to form granules, which were applied by spraying.

EXAMPLE 10

(Granules)

95 parts of clay particles with a particle-size distribution of 0.2 – 2 mm were charged into a rotary mixer and during rotation a solution of 5 parts of compound No. 4 in an organic solvent was sprayed on the particles. The latter were dried at 40° – 50° C to form granules, which were applied by spraying.

EXAMPLE 11

(Oil preparation)

0.5 part of compound No. 5, 20 parts of Velsicol AR-50 (a methylnaphthalene) and 79.5 parts of Deobase (deodorized kerosene) were mixed and agitated to form an oil preparation. The latter was applied by sprinkling.

The pesticidal activity of the active compounds of the present invention can be illustrated by the following test Examples.

EXAMPLE 12

Test of effects against *Tetranychus urticae*

Preparation of sample preparation:
 Solvent: 3 parts by weight of xylol
 Emulsifying agent: 1 part by weight of alkylaryl polyglycol ether In order to form a suitable preparation of the active compound, 1 part by weight of the active compound was mixed with the aforesaid amount of solvent containing the aforesaid amount of emulsifying agent and this mixture was diluted with water to a predetermined concentration.

Testing method

Kidney-bean plants with two main leaves and which were cultivated in pots of 6 cm diameter, were infested with 50–100 spider mites (*Tetranychus urticae*, both imagines and nymphs) having resistance to conventional organophosphorus pesticides; 2 days later, each pot was sprinkled with 20 ml of an aqueous preparation containing a predetermined concentration of the active compound and which had been prepared as stated above, and was then placed in a greenhouse. Ten days later the control effect was evaluated in accordance with the following scale.

3: no living imagines and nymphs.
2: less than 5% of living imagines and nymphs compared with an untreated control.
1: 5–50% of living imagines and nymphs compared with an untreated control.
0: more than 50% of living imagines and nymphs compared with an untreated control.

The results are given in Table 1.

Table 1

| Compound | Concentration of Active Component (% by weight) | | |
|---|---|---|---|
| | 0.1 | 0.03 | 0.01 |
| 1 | 3 | 3 | 3 |
| 2 | 3 | 3 | 3 |
| 3 | 3 | 3 | 3 |
| 4 | 3 | .3 | 2 |
| 5 | 3 | 3 | 3 |
| 6 | 3 | 3 | 1 |
| 7 | 3 | 3 | 2 |
| Comparative Compound (A) | 2 | 0 | 0 |
| Comparative Compound (B) | 2 | 1 | 0 |
| Comparative Compound (C) | 1 | 0 | 0 |
| Comparative Compound (D) | 2 | 1 | 0 |
| [C₂H₅O structure] | 2 | 0 | 0 |

Comparative Compound (A):
$$\begin{array}{c} C_2H_5 \\ C_2H_5SCH_2CH_2S \end{array} \!\!\! \begin{array}{c} S \\ \| \\ P-O- \end{array} \!\! \text{(2,4-Cl}_2\text{C}_6\text{H}_3\text{)}$$

Comparative Compound (B):
$$\begin{array}{c} C_2H_5 \\ C_2H_5S \end{array} \!\!\! \begin{array}{c} S \\ \| \\ P-O- \end{array} \!\! \text{(2,4-Cl}_2\text{C}_6\text{H}_3\text{)}$$

Comparative Compound (C):
$$\begin{array}{c} C_2H_5 \\ C_2H_5SCH_2CH_2S \end{array} \!\!\! \begin{array}{c} S \\ \| \\ P-O- \end{array} \!\! \text{(2-Cl-C}_6\text{H}_4\text{)}$$

Comparative Compound (D):
$$\begin{array}{c} C_2H_5 \\ C_2H_5SCH_2CH_2S \end{array} \!\!\! \begin{array}{c} S \\ \| \\ P-O- \end{array} \!\! \text{(4-SCH}_3\text{-C}_6\text{H}_4\text{)}$$

$$\begin{array}{c} C_2H_5O \\ C_2H_5O \end{array} \!\!\! \begin{array}{c} S \\ \| \\ P-O- \end{array} \!\! \text{(2,4-Cl}_2\text{C}_6\text{H}_3\text{)}$$

Table 1-continued

| Compound | Concentration of Active Component (% by weight) | | |
|---|---|---|---|
| | 0.1 | 0.03 | 0.01 |
| Comparative Compound (E) | | | |

Note:
1. Comparative Compound (B) is disclosed in Japanese Patent Publication No. 24874/63
2. Comparative Compounds (C) and (D) are disclosed in German Patent Specification No. 1954894
3. Comparative Compound (E) has the trade-name "Nemacide".

EXAMPLE 13

Test of effects against *Prodenia litura*

Testing Method:

Sweet-potato leaves were dipped into a preparation containing a predetermined concentration of the active compound and which was prepared according to the procedure described in Example 12. After drying the leaves in air, they were put into Petri dishes of 9 cm in diameter. 10 third-instar *Prodenia litura* larvae were placed in each dish, which was then maintained at a temperature of 28° C. 24 hours later the number of dead insects was counted in order to determine the mortality as a percentage.

The results are given in Table 2.

Table 2

| Compound | Mortality (%) at a Concentration of Active Component (by weight) of | | |
|---|---|---|---|
| | 0.1% | 0.03% | 0.01% |
| 1 | 100 | 100 | 20 |
| 2 | 100 | 100 | 50 |
| 3 | 100 | 80 | 20 |
| 4 | 100 | 70 | 10 |
| 5 | 100 | 40 | 10 |
| 6 | 100 | 90 | 30 |
| 7 | 100 | 100 | 60 |
| Comparative Compound (A) | 0 | 0 | 0 |
| Comparative Compound (B) | 20 | 0 | 0 |
| Comparative Compound (C) | 0 | 0 | 0 |
| Comparative Compound (D) | 0 | 0 | 0 |
| Comparative Compound (E) | 50 | 0 | 0 |

EXAMPLE 14

Test of effects against *Plutella maculipennis*

Testing Method:

Cabbage leaves were dipped into a preparation containing a predetermined concentration of the active compound and which was prepared following the procedure described in Example 12. After drying in air, the leaves were put into Petri dishes 9 cm in diameter, 10 *Plutella maculipennis* larvae were put into each dish, which was then placed in a room at a constant temperature of 28° C. 48 hours later the number of dead insects was counted in order to determine the mortality as a percentage. The results are given in Table 3.

Table 3

| Compound | Mortality (%) at a Concentration of Active Component (by weight) of | | |
|---|---|---|---|
| | 0.1% | 0.01% | 0.001% |
| 1 | 100 | 100 | 85 |
| 2 | 100 | 100 | 60 |
| 3 | 100 | 100 | 40 |
| 4 | 100 | 100 | 70 |
| 5 | 100 | 100 | 0 |
| 6 | 100 | 100 | 0 |
| 7 | 100 | 100 | 90 |
| Comparative Compound (A) | 70 | 0 | 0 |
| Comparative Compound (B) | 90 | 0 | 0 |
| Comparative Compound (C) | 40 | 0 | 0 |
| Comparative Compound (D) | 100 | 20 | 0 |
| Comparative Compound (E) | 90 | 10 | 0 |

EXAMPLE 15

Test of effects against *Musca domestica*

Testing Method:

Filter paper was spread on a Petri dish 9 cm in diameter and 1 ml of a preparation, containing a predetermined concentration of the active compound and which was prepared following the procedure described in Example 12, were added. 10 *Musca domestica* female imagines were put into the dish, which was then placed in a room at a constant temperature of 28° C. 24 hours later the number of dead insects was counted in order to determine the mortality as a percentage. The results are shown in Table 4.

Table 4

| Compound | Mortality (%) at a Concentration of Active Component (by weight) of | |
|---|---|---|
| | 0.1% | 0.01% |
| 1 | 100 | 80 |
| 2 | 100 | 100 |
| 3 | 100 | 100 |
| 4 | 100 | 90 |
| 5 | 100 | 100 |
| 6 | 100 | 100 |
| 7 | 100 | 80 |
| Comparative Compound (A) | 50 | 0 |
| Comparative Compound (B) | 100 | 30 |
| Comparative Compound (C) | 10 | 0 |
| Comparative Compound (D) | 80 | 0 |

EXAMPLE 16

Test of effects against *Meloidogyne incognita*

Preparation of sample formulation:

2 parts by weight of the active compound and 98 parts by weight of talc were mixed and the mixture was ground to form a dust.

Test Procedure

The active-compound formulation was mixed with soil (which had been tainted with sweet-potato root knot nematodes) in an amount such that a given concentration of the active compound was obtained in the soil. The treated soil was stirred until uniform, and was then packed into pots, each having an area of 1/5000 are. About 20 tomato seeds were sown per pot and cultivated for 4 weeks in a greenhouse. Then each tomato plant was drawn out from the soil without damaging the roots. The infestation grade caused by the nematodes was evaluated, with respect to 10 tomato plants as one group, on the following scale.

Knot Index

0—no knot (perfect control)
1—knots are formed to a slight degree
2—knots are formed to a moderate degree
3—knots are formed to a considerable degree
4—formation of knots is extreme The infestation grade was determined by the following equation:

$$\text{Infestation grade} = \frac{\Sigma(\text{rank value}) \times (\text{rank population})}{(\text{whole population examined}) \times 4} \times 100$$

The results are shown in Table 5:

Table 5

| Compound | Infestation grade (%) at at Concentration of Active Component of | | |
|---|---|---|---|
| | 50 ppm | 25 ppm | 10 ppm |
| 1 | 0 | 0 | 18.8 |
| 2 | 0 | 0 | 2.5 |
| 3 | 0 | 0 | 15.0 |
| 4 | 0 | 0 | 30.0 |
| 5 | 0 | 3.8 | 26.7 |
| 6 | 0 | 4.3 | 18.7 |
| 7 | 0 | 4.0 | 22.2 |

It will be appreciated that the instant specification and examples are set forth by way of illustration and not limitation, and that various modifications and changes may be made without departing from the spirit and scope of the present invention.

What is claimed is:

1. The method of combating pests selected from the group consisting of insects, acarids and nematodes which comprises applying to such pests or their habitat an insecticidally, acaricidally or nematocidally effective amount of a di- or trithiophosphonic acid ester of the formula

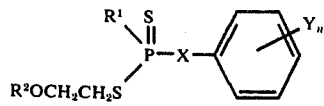

in which
R$^1$ and R$^2$ each independently is C$_1$-C$_6$ alkyl,
X is oxygen or sulfur,
Y is C$_1$-C$_6$ alkyl, C$_1$-C$_6$ alkylmercapto or halogen, and
n is 1 or 2.

2. A methyl according to claim 1, in which R$^1$ and R$^2$ each is C$_1$-C$_4$ alkyl, and Y is C$_1$-C$_4$ alkyl, C$_1$-C$_4$ alkylmercapto or halogen.

3. The method according to claim 1 in which said compound is O-(2,4-dichlorophenyl)-S-(2-ethoxyethyl)-methane-phosphonodithioate of the formula

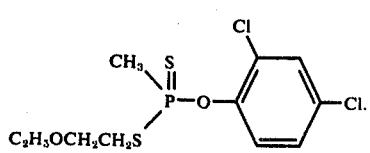

4. The method according to claim 1 in which said compound is O-(2,4-dichlorophenyl)-S-(2-isopropoxyethyl)-methane-phosphonodithioate of the formula

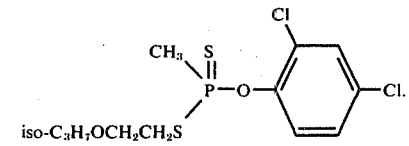

5. The method according to claim 1 in which said compound is O-(4-methylmercaptophenyl)-S-(2-ethoxyethyl)-ethane-phosphonodithioate of the formula

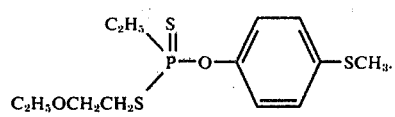

6. The method according to claim 1 in which said compound is O-(2-chloro-4-tert.-butylphenyl)-S-(2-ethoxyethyl)-methane-phosphonodithioate of the formula

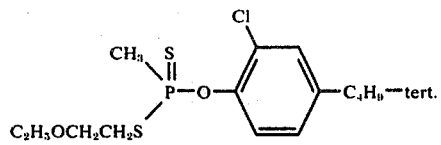

7. The method according to claim 1 in which said compound is S-(4-chlorophenyl)-S-(2-ethoxyethyl)-methane-phosphonotrithioate of the formula

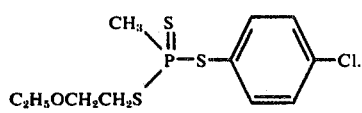

8. The method according to claim 1 in which said compound is S-(4-chlorophenyl)-S-(2-ethoxyethyl)-ethane-phosphonotrithioate of the formula

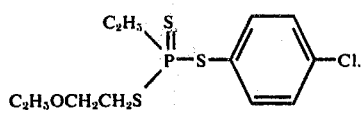

9. The method according to claim 1 in which said compound is O-(2,4-dichlorophenyl)-S-(2-ethoxyethyl)-ethane-phosphonodithioate of the formula

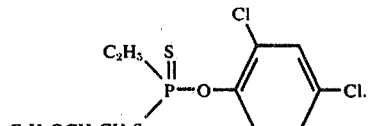

10. An insecticidal, acaricidal or nematocidal composition comprising an insecticidally, acaricidally or nematocidally effective amount of a compound of the formula

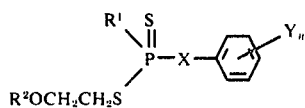

in which
R¹ and R² each independently is $C_1$-$C_6$ alkyl,
X is oxygen or sulfur,
Y is $C_1$-$C_6$ alkyl, $C_1$-$C_6$ alkylmercapto or halogen, and
n is 1 or 2,
in admixture with a diluent.

11. The composition according to claim 10, in which said compound is:
O-(2,4-dichlorophenyl)-S-(2-ethoxyethyl)-methane-phosphonodithioate,
O-(2,4-dichlorophenyl)-S-(2-isopropoxyethyl)-methane-phosphonodithioate,
O-(4-methylmercaptophenyl)-S-(2-ethoxyethyl)-ethane-phosphonodithioate,
O-(2-chloro-4-tert.-butylphenyl)-S-(2-ethoxyethyl)-methane-phosphonodithioate,
S-(4-chlorophenyl)-S-(2-ethoxyethyl)-methane-phosphono-trithioate, or
S-(4-chlorophenyl)-S-(2-ethoxyethyl)-ethane-phosphono-trithioate.

* * * * *